US008357395B2

(12) United States Patent
Bunick et al.

(10) Patent No.: US 8,357,395 B2
(45) Date of Patent: Jan. 22, 2013

(54) MANUFACTURE OF TABLET

(75) Inventors: Frank J. Bunick, Randolph, NJ (US); Joseph Luber, Quakertown, PA (US); Stephen A. Ulrich, Cherry Hill, NJ (US); David W. Wynn, Huntingdon Valley, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 873 days.

(21) Appl. No.: 12/336,812

(22) Filed: Dec. 17, 2008

(65) Prior Publication Data
US 2009/0162435 A1 Jun. 25, 2009

Related U.S. Application Data

(60) Provisional application No. 61/015,684, filed on Dec. 21, 2007.

(51) Int. Cl.
*A61K 9/20* (2006.01)
*A61K 9/28* (2006.01)

(52) U.S. Cl. .......................... 424/464; 424/474

(58) Field of Classification Search .................. 424/464, 424/474
See application file for complete search history.

(56) References Cited

U.S. PATENT DOCUMENTS

| | | | |
|---|---|---|---|
| 3,185,626 A | 5/1965 | Baker | |
| 3,647,333 A * | 3/1972 | Smith | 425/78 |
| 4,173,626 A | 11/1979 | Dempski et al. | |
| 4,543,370 A | 9/1985 | Porter et al. | |
| 4,643,894 A | 2/1987 | Porter et al. | |
| 4,683,256 A | 7/1987 | Porter et al. | |
| 4,725,441 A | 2/1988 | Porter et al. | |
| 4,802,924 A | 2/1989 | Woznicki et al. | |
| 4,828,841 A | 5/1989 | Porter et al. | |
| 4,851,226 A | 7/1989 | Julian et al. | |
| 4,863,742 A | 9/1989 | Panoz et al. | |
| 4,865,789 A | 9/1989 | Castro et al. | |
| 4,906,478 A | 3/1990 | Valentine et al. | |
| 4,980,170 A | 12/1990 | Schneider et al. | |
| 4,984,240 A | 1/1991 | Keren-Zvi et al. | |
| 5,075,114 A | 12/1991 | Roche | |
| 5,275,822 A | 1/1994 | Valentine et al. | |
| 5,286,497 A | 2/1994 | Hendrickson et al. | |
| 5,489,436 A | 2/1996 | Hoy | |
| 5,501,861 A * | 3/1996 | Makino et al. | 424/464 |
| 5,609,883 A | 3/1997 | Valentine | |
| 5,629,022 A | 5/1997 | Perovitch et al. | |
| 5,630,871 A | 5/1997 | Jordan | |
| 5,658,589 A | 8/1997 | Parekh | |
| 5,912,013 A | 6/1999 | Rudnic | |
| 6,103,260 A | 8/2000 | Luber | |
| 6,270,805 B1 | 8/2001 | Chen | |
| 6,274,162 B1 | 8/2001 | Steffenino | |
| 6,322,819 B1 | 11/2001 | Burnside | |
| 6,514,518 B2 | 2/2003 | Monkhouse | |
| 6,767,200 B2 * | 7/2004 | Sowden et al. | 425/345 |
| 7,122,143 B2 | 10/2006 | Sowden | |
| 7,217,381 B2 | 5/2007 | Sowden | |
| 7,300,668 B2 | 11/2007 | Pryce Lewis et al. | |
| 2004/0005360 A1 | 1/2004 | Wang et al. | |
| 2004/0156902 A1 * | 8/2004 | Lee et al. | 424/473 |
| 2005/0129746 A1 | 6/2005 | Lee et al. | |
| 2005/0129763 A1 | 6/2005 | Sowden | |
| 2005/0147677 A1 | 7/2005 | Sowden | |
| 2005/0152970 A1 | 7/2005 | Rinker et al. | |
| 2005/0249807 A1 | 11/2005 | Brown et al. | |

FOREIGN PATENT DOCUMENTS

EP 0146740 A 7/1985
EP 0468121 A 1/1992

OTHER PUBLICATIONS

Manna, Luigi et al. "Impregnation of PVP microparticles with ketoprofen in the presence of supercritical CO2", J. of Supercritical Fluids, 42, 2007, 378-384. Published Jan. 2, 2007.*
L. Manna et al. : "Impregnation of PVP microparticles with ketoprofen in the presence of supercritical CO2" Journal of Supercritical Fluids, vol. 42, 2007, pp. 378-384, XP022145402.
T. Comoglu et al.: "The effect of pressure and direct compression on tabletting of microsponges" International Journal of Pharmaceutics. vol. 242, 2002, pp. 191-195, XP008114062.
Database WPI Week 200679 Thomsom Scientific. London, GB; AN 771253, XP002552685 & JP 2006 273824A (Kobayashi Pharm Co. Ltd) Oct. 12, 2006.
USP24, pp. 19-20 (2000) and pp. 856-857 (1999).
The Theory and Practice of Industrial Pharmacy, Chapter 11 (3rd ed., Lea & Febiger, 1986).
"The Elizabeth Companies Tablet Design Training Manual" (Elizabeth Carbide Die Co., Inc., p. 7 (McKeesport, Pa.), Nov. 14, 2002.
Pharmaceutical Dosage Forms—Tablets, vol. 2, 2nd ed., Marcel Dekker Inc., 1990, pp. 213-217, 327-329.

* cited by examiner

*Primary Examiner* — Richard Schnizer
*Assistant Examiner* — Audrea Buckley
(74) *Attorney, Agent, or Firm* — William E. McGowan

(57) ABSTRACT

The present invention features a method of manufacturing a tablet containing a pharmaceutically active agent by the steps of: (a) adding a powder containing a pharmaceutically-acceptable carrier to a die cavity; (b) injecting a liquid drug composition containing the pharmaceutically active agent into the die cavity such that the liquid drug composition contacts the powder; (c) compressing the combination of the powder and the liquid drug composition within the die cavity to form the tablet; and (d) removing the tablet from the die cavity.

19 Claims, No Drawings

MANUFACTURE OF TABLET

CROSS-REFERENCE TO RELATED APPLICATIONS

This Application claims priority to U.S. Provisional Patent Application No. 61/015,684, filed on Dec. 21, 2007, which is hereby incorporated by reference in its entirety.

BACKGROUND OF THE INVENTION

Compressed tablets (e.g., caplets) are known as one of the most cost effective, consumer friendly and convenient dosage forms available for delivering pharmaceutically active agents. Compressed tablets often involve multiple steps in order to incorporate pharmaceutically active agents into the form since only certain materials may be used for compression. The materials must have the correct compression characteristics such as flow and compressibility in order to maintain operability on a tablet press, retain shape and form without breakage, and dissolve within an appropriate timeframe in the gastrointestinal tract. In order to achieve these characteristics, blends or powdered materials must often be granulated using high shear, chilsonation, or fluid bed techniques to increase the size and maintain a flowable particle shape. Methods for direct compression and wet granulation processes are known in the art, and are described in detail in, for example, Lachman, et al., *The Theory and Practice of Industrial Pharmacy*, Chapter 11 (3rd ed. 1986).

Traditional granulation techniques present additional challenges when a dosage form must be prepared with multiple pharmaceutically active agents. In many cases, it may be desired to combine large dose pharmaceutically active agents, such as acetaminophen, with smaller dose pharmaceutically active agents, such as chlorpheniramine or dextromethorphan. In order to achieve this, multiple types of granulations must often be prepared at a manufacturing scale, which increases cost and complexity. In addition to these challenges with granulation, the pharmaceutical industry has actively progressed in developing pharmaceutically active agents that require smaller and smaller doses, to the point where it is not uncommon for such agents to be administered at less than 1 microgram per dose. However, as the dose of the pharmaceutically active agent becomes smaller, the size of the tablet that is administered still remains relatively the same for ease of handling and swallowing. Therefore, in order to maintain uniformity of the agent within the compression blend, multiple blending steps are often required prior to compression.

The present invention provides for an improved method of manufacturing a tablet containing a pharmaceutically active agent by injecting a liquid drug composition containing the pharmaceutically active agent into the die cavity. The invention can provide for improved content uniformity in tablets that contain small quantities of pharmaceutically active agents, as liquid solutions are generally more uniform than powder mixtures. The invention also provides for the advantage of delivering to each tablet a precise quantity of pharmaceutically active agents, which can be difficult to achieve by conventional dry blending methodologies. Moreover, the present invention also can allow for greater efficiency and a more rapid change over between the manufacture of different tablets as a simple direct compression tablet base can be used for many different liquid injected pharmaceutically active agents.

SUMMARY OF THE INVENTION

In one aspect, the present invention features a method of manufacturing a tablet containing a pharmaceutically active agent by the steps of: (a) adding a powder containing a pharmaceutically-acceptable carrier to a die cavity; (b) injecting a liquid drug composition containing the pharmaceutically active agent into the die cavity such that the liquid drug composition contacts the powder; (c) compressing the combination of the powder and the liquid drug composition within the die cavity to form the tablet; and (d) removing the tablet from the die cavity.

In another aspect, the present invention features a method of manufacturing a tablet containing a pharmaceutically active agent by the steps of: (a) adding a powder to a die cavity; (b) compressing the powder within the die cavity to form a tablet; (c) injecting a liquid drug composition containing the pharmaceutically active agent onto the tablet while the tablet is still within the die cavity; and (d) removing the tablet from the die cavity.

Other features and advantages of the present invention will be apparent from the detailed description of the invention and from the claims.

DETAILED DESCRIPTION OF THE INVENTION

It is believed that one skilled in the art can, based upon the description herein, utilize the present invention to its fullest extent. The following specific embodiments can be construed as merely illustrative, and not limitative of the remainder of the disclosure in any way whatsoever.

Unless defined otherwise, all technical and scientific terms used herein have the same meaning as commonly understood by one of ordinary skill in the art to which the invention belongs. Also, all publications, patent applications, patents, and other references mentioned herein are incorporated by reference. As used herein, all percentages are by weight unless otherwise specified.

Manufacture of Tablet

In one aspect, the present invention features a method of manufacturing a tablet containing a pharmaceutically active agent by the steps of: (a) adding a powder containing a pharmaceutically-acceptable carrier to a die cavity; (b) injecting a liquid drug composition containing the pharmaceutically active agent into the die cavity such that the liquid drug composition contacts the powder; (c) compressing the combination of the powder and the liquid drug composition within the die cavity to form the tablet; and (d) removing the tablet from the die cavity. In one embodiment, the method further includes the step of adding additional powder to the die cavity after the step of injecting the liquid drug composition but prior to the step of compressing the combination. In a further embodiment, the additional powder is different from the powder initially added to the die cavity. In a further embodiment, the liquid portion of the liquid drug composition is removed from the composition, allowing for the pharmaceutically active agent to remain in the dosage form.

In another aspect, the present invention features a method of manufacturing a tablet containing a pharmaceutically active agent by the steps of: (a) adding a powder to a die cavity; (b) compressing the powder within the die cavity to form a tablet; (c) injecting a liquid drug composition containing the pharmaceutically active agent onto the tablet while the tablet is still within the die cavity; and (d) removing the tablet from the die cavity.

As discussed above, one benefit of the above methods is that the method is effective for manufacturing tablets having a low concentration of a pharmaceutically active agent. For example, in one embodiment, the concentration of the pharmaceutically active agent is less than about 10%, by weight, of the tablet, such as less than about 5%, by weight, of the tablet, such as less than about 1%, by weight, of the tablet, such as less than about 0.5%, by weight, of the tablet, such as less than about 0.1%, by weight, of the tablet.

In one embodiment, the powder further contains a pharmaceutically active agent, which may be the same or a different pharmaceutically active agent than the pharmaceutically active agent contained within the liquid drug composition.

In one embodiment of the invention, the powders having an average particle size of about 50 microns to about 500 microns, such as between 50 microns and 300 microns. Particles in this size range are particularly useful for direct compression processes.

In embodiment, the components of powder are blended together, for example as dry powders, and fed into the die cavity of an apparatus that applies pressure to form a tablet. Any suitable compacting apparatus may be used, including, but not limited to, conventional unitary or rotary tablet press. In one embodiment, the tablet may be formed by compaction using a rotary tablet press (e.g., such as those commercially available from Fette America Inc., Rockaway, N.J., or Manesty Machines LTD, Liverpool, UK). In general, a metered volume of powder is filled into a die cavity, where the powder is either gravity fed or mechanically fed from a feeder, of the rotary tablet press, and the cavity rotates as part of a "die table" from the filling position to a compaction position. At the compaction position, the powder is compacted between an upper and a lower punch, then the resulting tablet is pushed from the die cavity by the lower punch and then guided to an injection chute by a stationary "take-off" bar. Advantageously, the direct compression process enables the minimization or elimination of water-soluble, non-saccharide polymeric binders such as polyvinyl pyrrolidone, alginates, hydroxypropyl cellulose, hydroxypropylmethylcellulose, hydroxyethylcellulose, which could have a negative effect on dissolution.

In another embodiment, the tablet may be prepared by the compression methods and apparatus described in United States Patent Application Publication No. 20040156902. Specifically, the tablet may be made using a rotary compression module including a fill zone, insertion zone, compression zone, ejection zone, and purge zone in a single apparatus having a double row die construction. The dies of the compression module may then be filled using the assistance of a vacuum, with filters located in or near each die. The purge zone of the compression module includes an optional powder recovery system to recover excess powder from the filters and return the powder to the dies.

In another embodiment, the tablet may be prepared by a wet-granulation method, in which the excipients and a solution or dispersion of a wet binder (e.g., an aqueous cooked starch paste or solution of polyvinyl pyrrolidone) are mixed and granulated. Suitable apparatus for wet granulation include low shear mixers (e.g., planetary mixers), high shear mixers, and fluid beds (including rotary fluid beds). The resulting granulated material may then be dried, and optionally dry-blended with further ingredients (e.g., excipients such as, for example, lubricants, colorants, and the like). The final dry blend is then suitable for compression by the methods described in the previous paragraph. Methods for direct compression and wet granulation processes are known in the art.

In one embodiment, the tablet is prepared by the compression methods and apparatus described in issued U.S. Pat. No. 6,767,200, the disclosure of which is incorporated herein by reference. Specifically, the tablet is made using a rotary compression module including a fill zone, compression zone, and ejection zone in a single apparatus having a double row die construction as shown in FIG. 6 therein. The dies of the compression module are preferably filled using the assistance of a vacuum, with filters located in or near each die.

In one embodiment of the invention, the tablet may be a directly compressed tablet made from a powder that is substantially free of water-soluble polymeric binders and hydrated polymers. As used herein, what is meant by "substantially free" is less than 5%, such as less than 1%, such as less than 0.1%, such as completely free (e.g., 0%). This composition is advantageous for maintaining an immediate release dissolution profile, minimizing processing and material costs, and providing for optimal physical and chemical stability of the tablet. In one embodiment the density of the tablet is greater than about 0.9 g/cc.

The tablet may have one of a variety of different shapes. For example, the tablet may be shaped as a polyhedron, such as a cube, pyramid, prism, or the like; or may have the geometry of a space figure with some non-flat faces, such as a cone, truncated cone, cylinder, sphere, torus, or the like. In certain embodiments, a tablet has one or more major faces. For example, the tablet surface typically has opposing upper and lower faces formed by contact with the upper and lower punch faces in the compression machine. In such embodiments the tablet surface typically further includes a "belly-band" located between the upper and lower faces, and formed by contact with the die walls in the compression machine. A tablet may also be a multilayer tablet.

Exemplary tablet shapes that may be employed include tablet shapes formed from compression tooling shapes described by "The Elizabeth Companies Tablet Design Training Manual" (Elizabeth Carbide Die Co., Inc., p. 7 (McKeesport, Pa.) (incorporated herein by reference) as follows (the tablet shape corresponds inversely to the shape of the compression tooling): 1. Shallow Concave. 2. Standard Concave. 3. Deep Concave. 4. Extra Deep Concave. 5. Modified Ball Concave. 6. Standard Concave Bisect. 7. Standard Concave Double Bisect. 8. Standard Concave European Bisect. 9. Standard Concave Partial Bisect. 10. Double Radius. 11. Bevel & Concave. 12. Flat Plain. 13. Flat-Faced-Beveled Edge (F.F.B.E.). 14. F.F.B.E. Bisect. 15. F.F.B.E. Double Bisect. 16. Ring. 17. Dimple. 18. Ellipse. 19. Oval. 20. Capsule. 21. Rectangle. 22. Square. 23. Triangle. 24. Hexagon. 25. Pentagon. 26. Octagon. 27. Diamond. 28. Arrowhead. 29. Bullet. 30. Shallow Concave. 31. Standard Concave. 32. Deep Concave. 33. Extra Deep Concave. 34. Modified Ball Concave. 35. Standard Concave Bisect. 36. Standard Concave Double Bisect. 37. Standard Concave European Bisect. 38. Standard Concave Partial Bisect. 39. Double Radius. 40. Bevel & Concave. 41. Flat Plain. 42. Flat-Faced-Beveled Edge (F.F.B.E.). 43. F.F.B.E. Bisect. 44. F.F.B.E. Double Bisect. 45. Ring. 46. Dimple. 47. Ellipse. 48. Oval. 49. Capsule. 50. Rectangle. 51. Square. 52. Triangle. 53. Hexagon. 54. Pentagon. 55. Octagon. 56. Diamond. 57. Arrowhead. 58. Bullet. 59. Barrel. 60. Half Moon. 61. Shield. 62. Heart. 63. Almond. 64. House/Home Plate. 65. Parallelogram. 66. Trapezoid. 67. Bar Bell. 68. Bow Tie. 69. Uneven Triangle.

Alternatively, if tablets of the same composition are to be used in the dosage forms, the compression module may be equipped with multi-tip compression tooling. Four-tip tooling, for example, may be used to make four tablets within one die. The tablets may contain a single layer of multiple layers.

In certain embodiments, multilayer tablets can be produced with the invention described herein (e.g., bi-layer or tri-layer tablets can be produced). In one embodiment, the tablet die is filled with a first portion of the powder, the liquid drug composition is injected into the die cavity, the powder bed is optionally compressed a first time, a second portion of the powder is added, the tablet is compressed, and the tablet is ejected from the die. In one embodiment, the second portion of powder has the same blend composition as the first portion of powder. In another embodiment, the second portion of powder has a different composition from the first portion of powder. In one embodiment the first portion of the powder contains a pharmaceutically active agent and the second portion of the powder contains a different pharmaceutically active agent. In one embodiment, the first portion is for immediate release and the second portion is for modified release.

The liquid drug composition may be injected from a variety of configurations within the tablet press. The injection port for injecting the liquid drug composition may be positioned above the die as an external addition to the tablet press for injection of the liquid drug compositions following the filling of the lower punch. In this case, the injection would take place from a vertical position. The injection port may also be integrated into various parts which come in contact with the tablet powder bed, including vertical positioning within the lower punch or upper punch, or as horizontal positioning within the die or the take-off bar. In one embodiment, wherein the injection port is integrated into the tablet tooling (punch or die), a separate cover closes off the injection port in order to prevent powder from contaminating or clogging the injection port. In one embodiment, the cover is a mesh screen which allows air to escape but prevents particles below the mesh size from entering the port.

In one embodiment the injector that delivers the liquid drug composition is metered via an electronically controlled valve. In this case, when the injector is energized, an electromagnet moves a plunger that opens the valve, allowing a portioned amount of liquid to squirt through a nozzle. In this embodiment the injector is controlled by a microprocessor. In one embodiment, the nozzle is designed to atomize the liquid to disperse it across a certain area over the tablet powder bed within the die. In a separate embodiment, the injector is mechanically actuated. In another embodiment, the injector is pneumatically actuated. In another embodiment, the injector contains a separate syringe that measures the liquid for delivery into the die.

In embodiments wherein a portion of the liquid drug composition is removed, the composition of the tablet or resulting tablet may be dried in a variety of means, including, but not limited to, irradiative heating, microwave heating, infrared heating, or convective heating within a fluid bed dryer or a tablet coating pan.

Powder

As discussed above, the tablet is manufactured by compressing a powder containing a pharmaceutically-acceptable carrier. The carrier may contain one or more suitable excipients for the formulation of tablets. Examples of suitable excipients include, but are not limited to, fillers, adsorbents, binders, disintegrants, lubricants, glidants, release-modifying excipients, sweeteners, superdisintegrants, flavor and aroma agents, antioxidants, texture enhancers, and mixtures thereof.

Suitable fillers include, but are not limited to, water-soluble compressible carbohydrates such as sugars (e.g., dextrose, sucrose, maltose, and lactose), starches (e.g., corn starch), sugar-alcohols (e.g., mannitol, sorbitol, maltitol, and xylito), starch hydrolysates (e.g., dextrins, and maltodextrins), and water insoluble plastically deforming materials (e.g., microcrystalline cellulose or other cellulosic derivatives), and mixtures thereof.

Suitable adsorbents (e.g., to adsorb the liquid drug composition) include, but are not limited to, water-insoluble adsorbents such as dicalcium phosphate, tricalcium phosphate, silicified microcrystalline cellulose (e.g., such as distributed under the PROSOLV brand (PenWest Pharmaceuticals, Patterson, N.Y.)), magnesium aluminometasilicate (e.g., such as distributed under the NEUSILIN brand (Fuji Chemical Industries (USA) Inc., Robbinsville, N.J.), clays, silicas, bentonite, zeolites, magnesium silicates, hydrotalcite, veegum, and mixtures thereof.

Suitable binders include, but are not limited to, dry binders such as polyvinyl pyrrolidone and hydroxypropylmethylcellulose; wet binders such as water-soluble polymers, including hydrocolloids such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, and starches; and mixtures thereof.

Suitable disintegrants include, but are not limited to, sodium starch glycolate, cross-linked polyvinylpyrrolidone, cross-linked carboxymethylcellulose, starches, microcrystalline cellulose, and mixtures thereof.

Suitable lubricants include, but are not limited to, long chain fatty acids and their salts, such as magnesium stearate and stearic acid, talc, glycerides waxes, and mixtures thereof.

Suitable glidants include, but are not limited to, colloidal silicon dioxide.

Suitable release-modifying excipients include, but are not limited to, swellable erodible hydrophilic materials, insoluble edible materials, pH-dependent polymers, and mixtures thereof.

Suitable swellable erodible hydrophilic materials for use as release-modifying excipients include, but are not limited to, water swellable cellulose derivatives, polyalkylene glycols, thermoplastic polyalkylene oxides, acrylic polymers, hydrocolloids, clays, gelling starches, swelling cross-linked polymers, and mixtures thereof. Examples of suitable water swellable cellulose derivatives include, but are not limited to, sodium carboxymethylcellulose, cross-linked hydroxypropylcellulose, hydroxypropyl cellulose (HPC), hydroxypropylmethylcellulose (HPMC), hydroxyisopropylcellulose, hydroxybutylcellulose, hydroxyphenylcellulose, hydroxyethylcellulose (HEC), hydroxypentylcellulose, hydroxypropylethylcellulose, hydroxypropylbutylcellulose, and hydroxypropylethylcellulose, and mixtures thereof. Examples of suitable polyalkylene glycols include, but are not limited to, polyethylene glycol. Examples of suitable thermoplastic polyalkylene oxides include, but are not limited to, poly (ethylene oxide). Examples of suitable acrylic polymers include, but are not limited to, potassium methacrylatedivinylbenzene copolymer, polymethylmethacrylate, high-molecular weight cross-linked acrylic acid homopolymers and copolymers commercially available from Noveon Chemicals under the tradename, "CARBOPOL" (e.g., having a viscosity of greater than 50,000 centipoise when tested using a Brookfield RVT Viscometer at 25° C., using spindle #7, when dispersed in a basic solution). Examples of suitable hydrocolloids include, but are not limited to, alginates, agar, guar gum, locust bean gum, kappa carrageenan, iota carrageenan, tara, gum arabic, tragacanth, pectin, xanthan gum, gellan gum, maltodextrin, galactomannan, pusstulan, laminarin, scleroglucan, gum arabic, inulin, pectin, gelatin, whelan, rhamsan, zooglan, methylan, chitin, cyclodextrin, chitosan, and mixtures thereof. Examples of suitable clays include, but are not limited to, smectites such as bentonite, kaolin, and laponite; magnesium trisilicate; magnesium aluminum silicate; and mixtures thereof. Examples of suitable gelling starches include, but are not limited to, acid hydrolyzed starches, swelling starches such as sodium starch glycolate and derivatives thereof, and mixtures thereof. Examples of suitable swelling cross-linked polymers include, but are not limited to, cross-linked polyvinyl pyrrolidone, cross-linked agar, and cross-linked carboxymethylcellulose sodium, and mixtures thereof.

Suitable insoluble edible materials for use as release-modifying excipients include, but are not limited to, water-insoluble polymers and low-melting hydrophobic materials, copolymers thereof, and mixtures thereof. Examples of suitable water-insoluble polymers include, but are not limited to, ethylcellulose, polyvinyl alcohols, polyvinyl acetate, polycaprolactones, cellulose acetate and its derivatives, acrylates, methacrylates, acrylic acid copolymers, copolymers thereof, and mixtures thereof. Suitable low-melting hydrophobic materials include, but are not limited to, fats, fatty acid esters, phospholipids, waxes, and mixtures thereof. Examples of suitable fats include, but are not limited to, hydrogenated vegetable oils such as for example cocoa butter, hydrogenated palm kernel oil, hydrogenated cottonseed oil, hydrogenated sunflower oil, and hydrogenated soybean oil, free fatty acids and their salts, and mixtures thereof. Examples of suitable fatty acid esters include, but are not limited to, sucrose fatty acid esters, mono-, di-, and tri-glycerides, glyceryl behenate, glyceryl palmitostearate, glyceryl monostearate, glyceryl tristearate, glyceryl trilaurylate, glyceryl myristate, Glyco-Wax-932, lauroyl macrogol-32 glycerides, stearoyl macrogol-32 glycerides, and mixtures thereof. Examples of suitable phospholipids include phosphotidyl choline, phosphotidyl serene, phosphotidyl enositol, phosphotidic acid, and mixtures thereof. Examples of suitable waxes include, but are not limited to, carnauba wax, spermaceti wax, beeswax, candelilla wax, shellac wax, microcrystalline wax, and paraffin wax; fat-containing mixtures such as chocolate, and mixtures thereof.

Suitable pH-dependent polymers for use as release-modifying excipients include, but are not limited to, enteric cellulose derivatives such as hydroxypropyl methylcellulose phthalate, hydroxypropyl methylcellulose acetate succinate, cellulose acetate phthalate; natural resins such as shellac and zein; enteric acetate derivatives such as polyvinylacetate phthalate, cellulose acetate phthalate, acetaldehyde dimethylcellulose acetate; and enteric acrylate derivatives such as polymethacrylate-based polymers such as poly(methacrylate acid, methyl methacrylate) 1:2 (which is commercially available from Rohm Pharma GmbH under the tradename EUDRAGIT S), and poly(methacrylic acid, methyl methacrylate) 1:1 (which is commercially available from Rohm Pharma GmbH under the tradename EUDRAGIT L), and mixtures thereof.

Examples of suitable sweeteners include, but are not limited to, synthetic or natural sugars, sucralose, saccarin, sodium saccarin, aspartame, acesulfame K or acesulfame, potassium acesulfame, thaumatin, glycyrrhizin, dihydrochalcone, alitame, miraculin, monellin, stevside, and mixtures thereof.

Examples of superdisintegrants include, but are not limited to, croscarmellose sodium, sodium starch glycolate and cross-linked povidone (crospovidone). In one embodiment the tablet contains up to about 5% by weight of such superdisintegrant.

Examples of suitable flavor and aroma agents include, but are not limited to, essential oils including distillations, solvent extractions, or cold expressions of chopped flowers, leaves, peel or pulped whole fruit containing mixtures of alcohols, esters, aldehydes and lactones; essences including either diluted solutions of essential oils, or mixtures of synthetic chemicals blended to match the natural flavour of the fruit (e.g., strawberry, raspberry, and black currant); artificial and natural flavours of brews and liquors (e.g., cognac, whisky, rum, gin, sherry, port, and wine); tobacco, coffee, tea, cocoa, and mint; fruit juices including expelled juice from washed, scrubbed fruits such as lemon, orange, and lime; mint; ginger; cinnamon; cacoe/cocoa; vanilla; liquorice; menthol; eucalyptus; aniseeds nuts (e.g., peanuts, coconuts, hazelnuts, chestnuts, walnuts, and colanuts); almonds; raisins; and powder, flour, or vegetable material parts including tobacco plant parts (e.g., the genus *Nicotiana* in amounts not contributing significantly to a level of therapeutic nicotine), and mixtures thereof.

Examples of antioxidants include, but are not limited to, tocopherols, ascorbic acid, sodium pyrosulfite, butylhydroxytoluene, butylated hydroxyanisole, edetic acid, and edetate salts, and mixtures thereof. Examples of preservatives include, but are not limited to, citric acid, tartaric acid, lactic acid, malic acid, acetic acid, benzoic acid, and sorbic acid, and mixtures thereof.

Examples of texture enhancers include, but are not limited to, pectin, polyethylene oxide, and carageenan, and mixtures thereof. In one embodiment, texture enhancers are used at levels of from about 0.1% to about 10% percent by weight.

Liquid Drug Composition

As set forth above, the invention relates to injecting a liquid drug composition containing the pharmaceutically active agent. In one embodiment, the liquid drug composition is injected into the die cavity such that the liquid drug composition contacts the powder. In another embodiment, the liquid drug composition is injected into the die cavity such that the liquid drug composition contacts the tablet while the tablet is still within the die cavity.

The application and dispersion of the liquid into the powder bed may be controlled through parameters such as injection pressure, solution viscosity, and precise metering devices. The drug solution may be applied through an external metering device (e.g., syringe) held above the tablet die; or alternatively, through a metering device placed within the wall of the die cavity or the tip of the tablet punch.

Examples of liquid drug compositions include, but are not limited to, solutions and suspensions of the pharmaceutically active agent. In one embodiment, the liquid drug composition is a suspension of the pharmaceutically active agent, and the mean particle size of the pharmaceutically active agent is less than 100 microns.

In one embodiment, the liquid drug composition further contains a liquid carrier containing one or more liquid excipients. In one embodiment, the method further includes the step removing substantially all of the liquid excipeints from the tablet (e.g., at standard temperature and pressure or elevated temperature and/or reduced pressure). In one embodiment, the liquid excipient(s) are at least about 50 percent by weight of the total weight of the liquid drug composition (e.g., at least about 75 percent, such as at least about 85 percent).

Suitable liquid excipients for use in solutions and suspensions include, but are not limited to: water; polar organic solvents (such as methanol, ethanol, isopropanol, and acetone) and non-polar organic solvents (such as methylene chloride) and mixtures thereof. Other examples of liquid excipients include, but are not limited to, those that are not intended for removal from the tablet, such as propylene glycol, glycerin and polyethylene glycol, and mixtures thereof. In one embodiment the liquid carrier is in an oil which is liquid below 37° C., including, but not limited to, mineral oil, olive oil, corn oil, vegetable oil triglycerides and triacylglycerols, and vegetable oil, and mixtures thereof.

In one embodiment, the liquid carrier contains a liquid excipient that is a triglyceride (such as medium chain triglycerides), fractionated coconut oil, caprylic and capric triglycerides (such as those sold under the tradename Miglyol® 812 available from the Condea Vista Corporation), and mixtures thereof.

In one embodiment, the liquid carrier contains a liquid excipient that is a polydimethylsiloxanes. Examples of suitable polydimethylsiloxanes include, but are not limited to, dimethicone and simethicone, such as those disclosed in U.S. Pat. Nos. 4,906,478, 5,275,822, and 6,103,260. As used herein, the term "simethicone" refers to the broader class of polydimethylsiloxanes, including but not limited to simethicone and dimethicone.

In one embodiment, the liquid carrier includes the liquid excipient water and a gelling polymer, such as gelatin, carageenan, and gellan gum. In this embodiment, the die cavity is held at a temperature that is below the gelling temperature of the prepared solution or suspension. When the liquid is injected, the liquid carrier is then gelled, which can facilitate further handling of the dosage form.

The liquid drug composition may release the pharmaceutically active agent in an immediate release manner or a modified release manner. Thus, modified release materials may be added to the liquid drug composition (e.g., which form a modified release matrix upon drying in the tablet or in the case of a liquid molten composition, upon solidification). In one embodiment, particles containing the pharmaceutically active agent are prepared as a modified release particle (e.g., whereby the pharmaceutically active agent is bound to an ion exchange resin or coated with modified release coatings). In this embodiment, the modified release active particles as carried as a suspension in the liquid drug composition.

In one embodiment, a water insoluble polymer or pH dependent polymer is added to the liquid drug composition as a dispersion. In one embodiment the water insoluble polymer or pH dependent polymer is added to the liquid drug composition as a solution. Generally, a solution preparation containing a water insoluble polymer also contains an organic solvent. A solution preparation containing a pH dependent polymer may contain an organic solvent, an aqueous preparation at a pH level at which the pH dependent polymer will be solubilized, an aqueous buffer preparation, or a mixture thereof. In one embodiment, the liquid drug composition contains a combination of a water insoluble polymer and a pH dependent polymer.

In one embodiment, the liquid drug composition includes from about 0.05% to about 40% (e.g., from about 0.05 to about 20%, or from about 1.6 to about 10%, or from about 15 to about 40% weight per volume (w/v)) of at least one pharmaceutically active agent.

In one embodiment, the amount of the liquid drug composition that is injected into the die cavity is less than about 100 microliters (e.g., less than about 50 microliters or less than about 10 microliters). In one embodiment the amount of pharmaceutically active agent delivered in the injection into the die cavity, is less than about 1 milligram or less than about 0.5 milligrams, or less than about 0.1 milligrams.

The pharmaceutically active agent may be injected into the die cavity in a variety of crystal shapes or polymorphs. In one embodiment, the pharmaceutically active agent remains from about 100 percent in an amorphous state to about 50 percent in an amorphous state (e.g., 50 percent crystalline state). In certain embodiments, substantially all of the pharmaceutically active agent recrystallizes upon removal of the liquid excipients.

In one embodiment, the liquid excipeint is supercritical carbon dioxide (e.g., which evaporates upon injection) into the die cavity.

The liquid drug composition may also include viscosity enhancers, pH adjusting agents, plasticizers, sweeteners, flavor and aroma agents, release-modifying excipients, preservatives, antioxidants, and surfactants, and mixtures thereof.

Examples of viscosity enhancers include, but are not limited to, hydrophilic polymers such as hydrocolloids, swelling or gelling polymers, and mixtures thereof. In one preferred embodiment, the thickening component combines the attributes of a structuring agent. Examples of structuring agents include hydrocolloids, such as alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, karaya, whelan, rhamsan, zooglan, methylan, chitin, cyclodextrin, chitosan, and mixtures thereof. In certain embodiments of the present invention, xanthan gum is a preferred hydrocolloid for use as a structuring agent.

Examples of pH adjusting agents include, but are not limited to, organic acids, such as citric acid, malic acid, maleic acid, tartaric acid and lactic acid, and mixtures thereof. Other pH adjusting agents for use in the liquid drug composition include alkalizing agents such as potassium hydroxide, sodium hydroxide, magnesium hydroxide, calcium hydroxide, potassium acetate, sodium acetate, magnesium acetate, calcium carbonate, calcium oxide, calcium phosphates, magnesium carbonate, magnesium oxide, magnesium phosphates, magnesium hydroxide carbonate, magnesium aluminum silicate, magaldrate, dihydroxyaluminum sodium carbonate, ammonium hydroxide, ammonium bicarbonate, ammonium carbonate, ethanolamine, diethanolamine, triethanolamine, sodium bicarbonate, potassium bicarbonate, magnesium hydroxide, aluminum hydroxide, magnesium phosphates, tetrasodium ethylenediaminetetraacetic acid and its hydrates, and mixtures thereof.

Examples of plasticizers include, but are not limited to, sorbitol; triethyl citrate; tribuyl citrate; dibutyl sebecate and mixtures thereof.

Examples of preservatives include, but are not limited to, benzoic acid and its pharmaceutically acceptable salts, e.g. sodium benzoate; sorbic acid and its pharmaceutically acceptable salts, e.g. potassium sorbate; and parabens (such as methyl, ethyl, propyl and butyl p-hydroxybenzoic acids esters), and mixtures thereof.

Examples of surfactants include, but are not limited to, polysorbates made from the reaction product of monoglycerides or sorbitan esters with ethylene oxides. Examples of useful polysorbates include, but are not limited to, polyoxyethylene 20 mono- and diglycerides of saturated fatty acids, polyoxyethylene 4 sorbitan monostearate, polyoxyethylene 20 sorbitan tristearate, polyoxyethylene 20 sorbitan monooleate, polyoxyethylene 5 sorbitan monooleate, polyoxyethylene 20, sorbitan trioleate, sorbitan monopalmitate, sorbitan monolaurate, propylene glycol monolaurate, glycerol monostearate, diglycerol monostearate, glycerol lactylpalmitate, and mixtures thereof.

In one embodiment, the liquid drug composition includes a thixotrpic liquid. Thixotropic materials include materials that change in viscosity when subjected to certain stresses or forces (such as spraying, compression, or vibration). In the present invention, during the injecting step and/or during the compression step, the liquid drug composition containing the thixotropic material would increase in viscosity upon contact with the powder or tablet or under compression forces. Examples of thixotrpic materials include, but are not limited to, starches, modified starches, gums (such as xanthan gum, acacia gum, guar gum, locust bean gum, and tara gum), hydrophilic polymers (such as methyl cellulose, iota carageenan, and kappa carageenan, cross-linked synthetic polymers of acrylic acid (i.e. carbomers), sodium alginate and carboxymethyl cellulose), and solid materials such as clays and aluminum stearate, and mixtures thereof.

Molten Composition

In one embodiments of the invention, the liquid drug composition is a molten composition. In one embodiment, the molten composition contains a molten excipient that is liquid at a temperature between about 37° C. and 250° C., and that is solid or semi-solid at a temperature between below about 37° C. When it is in the liquid state, the molten composition may contain a solvent such as water or organic solvents, or combinations thereof. In one embodiment, the liquid drug composition is a molten composition (e.g., held above 30 degrees centigrade at the time of injection).

In one embodiment, the pharmaceutically active agent is dissolved or dispersed in the molten composition that is held in a liquid state at an elevated temperature during injection. Following injection, the molten composition solidifies upon contact with the powder or tablet, thus, in one embodiment, not requiring a further drying step. In one embodiment, the tablet powder or die cavity is held below 30° C. (such as below 25° C.) in order to facilitate hardening of the molten composition.

Suitable excipients for use in the molten composition include thermoplastic materials; film formers; thickeners (such as gelling polymers or hydrocolloids); low melting hydrophobic materials such as fats and waxes; and non-crystallizable carbohydrates, and mixtures thereof.

In one embodiment, the melting point of the pharmaceutically active agent is co-melted into the molten composition, since the temperature at which the molten composition is prepared and held is above the melting point of both the molten excipient(s) and the pharmaceutically active agent. In one embodiment, the percent of the molten composition is predominately a melted pharmaceutically active agent, wherein the pharmaceutically active agent is at least about 50 percent of the molten mixture, or at least about 75 percent or at least about 95 percent.

Examples of thermoplastic materials include, but are not limited to, both water-soluble and water insoluble polymers that are generally linear (not cross-linked, nor strongly hydrogen bonded to adjacent polymer chains), such as thermoplastic vinyl polymers, thermoplastic starches, thermoplastic polyalkalene glycols, thermoplastic polyalkalene oxides, and amorphous sugar-glass, and mixtures thereof.

Examples of suitable water swellable cellulose derivatives for use in the molten composition include, but are not limited to, hydroxypropyl cellulose (HPC), hydroxypropylmethyl cellulose (HPMC), methyl cellulose (MC), and mixtures thereof.

Examples of water insoluble cellulose derivatives for use in the molten composition include, but are not limited to, cellulose acetate (CA), ethyl cellulose (EC), cellulose acetate butyrate (CAB), cellulose propionate, and mixtures thereof. Examples of suitable thermoplastic vinyl polymers include polyvinyl alcohol (PVA) and polyvinyl pyrrolidone (PVP), and mixtures thereof.

Examples of suitable thermoplastic starches for use in the molten composition include, but are not limited to, those disclosed for example in U.S. Pat. No. 5,427,614. Examples of suitable thermoplastic polyalkalene glycols include, but are not limited to, polyethylene glycol (specifically polyetheylene glycols with a molecular weight at least about 1500 Daltons). Examples of suitable thermoplastic polyalkalene oxides include, but are not limited to, polyethylene oxide having a molecular weight from about 100,000 to about 900,000 Daltons. Other suitable thermoplastic materials include sugar in the form on an amorphous glass (such as that used to make hard candy forms).

Suitable low-melting hydrophobic materials for use as the molten excipients include, but are not limited to, fats, fatty acid esters, phospholipids, and waxes, and mixtures thereof. Examples of suitable fats include, but are not limited to, hydrogenated vegetable oils, such as cocoa butter, hydrogenated palm kernel oil, hydrogenated cottonseed oil, hydrogenated sunflower oil, and hydrogenated soybean oil; and free fatty acids and their salts, and mixtures thereof. Examples of suitable fatty acid esters include, but are not limited to, sucrose fatty acid esters, mono, di, and triglycerides, glyceryl behenate, glyceryl palmitostearate, glyceryl monostearate, glyceryl tristearate, glyceryl trilaurylate, glyceryl myristate, GlycoWax-932, lauroyl macrogol-32 glycerides, and stearoyl macrogol-32 glycerides, and mixtures thereof. Examples of suitable phospholipids include, but are not limited to, phosphotidyl choline, phosphotidyl serene, phosphotidyl enositol, and phosphotidic acid, and mixtures thereof. Examples of suitable waxes include, but are not limited to, carnauba wax, spermaceti wax, beeswax, candelilla wax, shellac wax, microcrystalline wax, and paraffin wax; fat-containing mixtures such as chocolate; and mixtures thereof.

Suitable non-crystallizable carbohydrates for use as a molten excipient or for use as part of the molten composition include, but are not limited to, non-crystallizable sugars such as polydextrose and starch hydrolysates (e.g. glucose syrup, corn syrup, and high fructose corn syrup; and non-crystallizable sugar-alcohols such as maltitol syrup), and mixtures thereof. Other suitable carbohydrates and carbohydrate alcohols for use as the molten excipient or for use as part of the molten composition include, but are not limited to, sucrose, fructose, glucose, isomalt, lactose, lactitol, sorbitol, mannitol, and mannose, and mixtures thereof.

In certain embodiments, the molten composition includes from about 20 percent to about 99.99 (such as from about 50 percent to about 99.5 percent) by weight of molten excipients.

Pharmaceutically Active Agent

The tablet of the present invention includes at least one pharmaceutically active agent. What is meant by a "pharmaceutically active agent" is an agent (e.g., a compound) that is permitted or approved by the U.S. Food and Drug Administration, European Medicines Agency, or any successor entity thereof, for the oral treatment of a condition or disease. Suitable pharmaceutically active agents include, but are not limited to, analgesics, anti-inflammatory agents, antihistamines, antibiotics (e.g., antibacterial, antiviral, and antifungal agents), antidepressants, antidiabetic agents, antispasmodics, appetite suppressants, bronchodilators, cardiovascular treating agents (e.g., statins), central nervous system treating agents, cough suppressants, decongestants, diuretics, expectorants, gastrointestinal treating agents, anesthetics, mucolytics, muscle relaxants, osteoporosis treating agents, stimulants, nicotine, and sedatives.

Examples of suitable gastrointestinal treating agents include, but are not limited to: antacids such as aluminum-containing pharmaceutically active agents (e.g., aluminum carbonate, aluminum hydroxide, dihydroxyaluminum sodium carbonate, and aluminum phosphate), bicarbonate-containing pharmaceutically active agents, bismuth-containing pharmaceutically active agents (e.g., bismuth aluminate, bismuth carbonate, bismuth subcarbonate, bismuth subgallate, and bismuth subnitrate), calcium-containing pharmaceutically active agents (e.g., calcium carbonate), glycine, magnesium-containing pharmaceutically active agents (e.g., magaldrate, magnesium aluminosilicates, magnesium carbonate, magnesium glycinate, magnesium hydroxide, magnesium oxide, and magnesium trisilicate), phosphate-containing pharmaceutically active agents (e.g., aluminum phosphate and calcium phosphate), potassium-containing pharmaceutically active agents (e.g., potassium bicarbonate), sodium-containing pharmaceutically active agents (e.g., sodium bicarbonate), and silicates; laxatives such as stool softeners (e.g., docusate) and stimulant laxatives (e.g., bisacodyl); H2 receptor antagonists, such as famotidine, ranitidine, cimetadine, and nizatidine; proton pump inhibitors such as omeprazole and lansoprazole; gastrointestinal cytoprotectives, such as sucraflate and misoprostol; gastrointestinal prokinetics such as prucalopride; antibiotics for *H. pylori*, such as clarithromycin, amoxicillin, tetracycline, and metronidazole; antidiarrheals, such as bismuth subsalicylate, kaolin, diphenoxylate, and loperamide; glycopyrrolate; analgesics, such as mesalamine; antiemetics such as ondansetron, cyclizine, diphenyhydroamine, dimenhydrinate, meclizine, promethazine, and hydroxyzine; probiotic bacteria including but not limited to lactobacilli; lactase; racecadotril; and antiflatulents such as polydimethylsiloxanes (e.g., dimethicone and simethicone, including those disclosed in U.S. Pat. Nos. 4,906,478, 5,275,822, and 6,103,260); isomers thereof, and pharmaceutically acceptable salts and prodrugs (e.g., esters) thereof.

Examples of suitable analgesics, anti-inflammatories, and antipyretics include, but are not limited to, non-steroidal anti-inflammatory drugs (NSAIDs) such as propionic acid derivatives (e.g., ibuprofen, naproxen, ketoprofen, flurbiprofen, fenbufen, fenoprofen, indoprofen, ketoprofen, fluprofen, pirprofen, carprofen, oxaprozin, pranoprofen, and suprofen) and COX inhibitors such as celecoxib; acetaminophen; acetyl salicylic acid; acetic acid derivatives such as indomethacin, diclofenac, sulindac, and tolmetin; fenamic acid derivatives such as mefanamic acid, meclofenamic acid, and flufenamic acid; biphenylcarbodylic acid derivatives such as diflunisal and flufenisal; and oxicams such as piroxicam, sudoxicam, isoxicam, and meloxicam; isomers thereof, and pharmaceutically acceptable salts and prodrugs thereof.

Examples of antihistamines and decongestants, include, but are not limited to, bromopheniramine, chlorcyclizine, dexbrompheniramine, bromhexane, phenindamine, pheniramine, pyrilamine, thonzylamine, pripolidine, ephedrine, phenylephrine, pseudoephedrine, phenylpropanolamine, chlorpheniramine, dextromethorphan, diphenhydramine, doxylamine, astemizole, terfenadine, fexofenadine, naphazoline, oxymetazoline, montelukast, propylhexadrine, triprolidine, clemastine, acrivastine, promethazine, oxomemazine, mequitazine, buclizine, bromhexine, ketotifen, terfenadine, ebastine, oxatamide, xylomeazoline, loratadine, desloratadine, and cetirizine; isomers thereof, and pharmaceutically acceptable salts and esters thereof.

Examples of cough suppressants and expectorants include, but are not limited to, diphenhydramine, dextromethorphan, noscapine, clophedianol, menthol, benzonatate, ethylmorphone, codeine, acetylcysteine, carbocisteine, ambroxol, belladona alkaloids, sobrenol, guaiacol, and guaifenesin; isomers thereof, and pharmaceutically acceptable salts and prodrugs thereof.

Examples of muscle relaxants include, but are not limited to, cyclobenzaprine and chlorzoxazone metaxalone, and orphenadrine, methocarbamol; isomers thereof, and pharmaceutically acceptable salts and prodrugs thereof.

Examples of stimulants include, but are not limited to, caffeine.

Examples of sedatives include, but are not limited to sleep aids such as antihistamines (e.g., diphenhydramine), eszopiclone, and zolpidem, and pharmaceutically acceptable salts and prodrugs thereof.

Examples of appetite suppressants include, but are not limited to, phenylpropanolamine, phentermine, and diethylcathinone, and pharmaceutically acceptable salts and prodrugs thereof.

Examples of anesthetics (e.g., for the treatment of sore throat) include, but are not limited to dyclonene, benzocaine, and pectin and pharmaceutically acceptable salts and prodrugs thereof.

Examples of suitable statins include but are not limited to atorvastin, rosuvastatin, fluvastatin, lovastatin, simvustatin, atorvastatin, pravastatin and pharmaceutically acceptable salts and prodrugs thereof.

In one embodiment, the pharmaceutically active agent included within the tabletis selected from phenylephrine, dextromethorphan, pseudoephedrine, acetaminophen, ibuprofen, ketoprofen, loperamide, famotidine, calcium carbonate, simethicone, and menthol, and pharmaceutically acceptable salts and prodrugs thereof.

In one embodiment, the pharmaceutically active agent is selected from phenylephrine, dextromethorphan, pseudoephedrine, chlorpheniramine, methocarbomal, chlophedianol, ascorbic acid, menthol, pectin, dyclonine, and benzocaine, and pharmaceutically acceptable salts and prodrugs thereof.

As discussed above, the pharmaceutically active agents of the present invention may also be present in the form of pharmaceutically acceptable salts, such as acidic/anionic or basic/cationic salts. Pharmaceutically acceptable acidic/anionic salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphospate, polygalacturonate, salicylate, stearate, subacetate, succinate, sulfate, tannate, tartrate, teoclate, tosylate and triethiodide. Pharmaceutically acceptable basic/cationic salts include, and are not limited to aluminum, benzathine, calcium, chloroprocaine, choline, diethanolamine, ethylenediamine, lithium, magnesium, meglumine, potassium, procaine, sodium and zinc.

As discussed above, the pharmaceutically active agents of the present invention may also be present in the form of prodrugs of the pharmaceutically active agents. In general, such prodrugs will be functional derivatives of the pharmaceutically active agent, which are readily convertible in vivo into the required pharmaceutically active agent. Conventional procedures for the selection and preparation of suitable prodrug derivatives are described, for example, in "Design of Prodrugs", ed. H. Bundgaard, Elsevier, 1985. In addition to salts, the invention provides the esters, amides, and other protected or derivatized forms of the described compounds.

Where the pharmaceutically active agents according to this invention have at least one chiral center, they may accordingly exist as enantiomers. Where the pharmaceutically active agents possess two or more chiral centers, they may additionally exist as diastereomers. It is to be understood that all such isomers and mixtures thereof are encompassed within the scope of the present invention. Furthermore, some of the crystalline forms for the pharmaceutically active agents may exist as polymorphs and as such are intended to be included in the present invention. In addition, some of the pharmaceutically active agents may form solvates with water (e.g., hydrates) or common organic solvents, and such solvates are also intended to be encompassed within the scope of this invention.

In one embodiment, the pharmaceutically active agent or agents are present in the tablet in a therapeutically effective amount, which is an amount that produces the desired therapeutic response upon oral administration and can be readily determined by one skilled in the art. In determining such amounts, the particular pharmaceutically active agent being administered, the bioavailability characteristics of the pharmaceutically active agent, the dose regime, the age and weight of the patient, and other factors must be considered, as known in the art.

The pharmaceutically active agent may be present in various forms. For example, the pharmaceutically active agent may be dispersed at the molecular level, e.g. melted, within the tablet, or may be in the form of particles, which in turn may be coated or uncoated. If the pharmaceutically active agent is in form of particles, the particles (whether coated or uncoated) typically have an average particle size of from about 1 to about 2000 microns. In one embodiment, such particles are crystals having an average particle size of from about 1 to about 300 microns. In another embodiment, the particles are granules or pellets having an average particle size of from about 50 to about 2000 microns, such as from about 50 to about 1000 microns, such as from about 100 to about 800 microns.

If the pharmaceutically active agent has an objectionable taste, the pharmaceutically active agent may be coated with a taste masking coating, as known in the art. Examples of suitable taste masking coatings are described in U.S. Pat. No. 4,851,226, U.S. Pat. No. 5,075,114, and U.S. Pat. No. 5,489,436. Commercially available taste masked pharmaceutically active agents may also be employed. For example, acetaminophen particles, which are encapsulated with ethylcellulose or other polymers by a coaccervation process, may be used in the present invention. Coaccervation-encapsulated acetaminophen may be purchased commercially from Eurand America, Inc. (Vandalia, Ohio) or from Circa Inc. (Dayton, Ohio).

The pharmaceutically active agent may be present in pure crystal form or in a granulated form prior to the addition of the taste masking coating. Granulation techniques may be used to improve the flow characteristics or particle size of the pharmaceutically active agents to make it more suitable for compression or subsequent coating. Suitable binders for making the granulation include but are not limited to starch, polyvinylpyrrolidone, polymethacrylates, hydroxypropylmethylcellulose, and hydroxypropylcellulose. The particles including pharmaceutically active agent(s) may be made by cogranulating the pharmaceutically active agent(s) with suitable substrate particles via any of the granulation methods known in the art. Examples of such granulation method include, but are not limited to, high sheer wet granulation and fluid bed granulation such as rotary fluid bed granulation, the details of which are disclosed in, "The Theory and Practice of Industrial Pharmacy, $3^{rd}$ edition", Chapter 11, Lachman, Leon et. al, 1986.

In one embodiment the orally disintegrating form of this invention incorporates gel-coated liquid filled beads, which may contain a flavorant, an pharmaceutically active agent or mixtures thereof. In one embodiment the gel-filled beads are coated with materials that include, but not limited to, hydrocolloids (such as acacia, alginates, agar, guar gum, locust bean, carrageenan, carboxymethylcellulose, tara, gum arabic, tragacanth, pectin, xanthan, gellan, gelatin, maltodextrin, galactomannan, pusstulan, laminarin, scleroglucan, inulin, whelan, rhamsan, zooglan, methylan, chitin, cyclodextrin, chitosan, polyvinyl pyrrolidone, cellulosics, sucrose, starches, and mixtures thereof, and a plasticizer (such as propylene glycol, glycerin or mixtures thereof). Since, in one embodiment, the tablet disclosed herein does not undergo a compression step, the gel-coated liquid filled beads are less likely break.

In one embodiment, the tablet incorporates modified release coated particles (e.g., particles containing at least one pharmaceutically active agent that convey modified release properties of such agent). As used herein, "modified release" shall apply to the altered release or dissolution of the active agent in a dissolution medium, such as gastrointestinal fluids. Types of modified release include, but are not limited to, extended release or delayed release. In general, modified release tablets are formulated to make the active agents(s) available over an extended period of time after ingestion, which thereby allows for a reduction in dosing frequency compared to the dosing of the same active agent(s) in a conventional tablet. Modified release tablets also permit the use of active agent combinations wherein the duration of one pharmaceutically active agent may differ from the duration of another pharmaceutically active agent. In one embodiment the tablet contains one pharmaceutically active agent that is released in an immediate release manner and an additional active agent or a second portion of the same active agent as the first that is modified release.

In one embodiment the pharmaceutically active agent is coated with a combination of a water insoluble film forming polymer (such as but not limited to cellulose acetate or ethylcellulose) and a water soluble polymer (such as but not limited to povidone, polymethacrylic co-polymers such as those sold under the tradename Eudragit E-100 from Rohm America, and hydroxypropylcellulose). In this embodiment, the ratio of water insoluble film forming polymer to water soluble polymer is from about 50 to about 95 percent of water insoluble polymer and from about 5 to about 50 percent of water soluble polymer, and the weight percent of the coating by weight of the coated taste-masked particle is from about 5 percent to about 40 percent.

In one embodiment one or more pharmaceutically active agents or a portion of the pharmaceutically active agent may be bound to an ion exchange resin for the purposes of taste-masking the pharmaceutically active agent or delivering the active in a modified release manner.

In one embodiment, the pharmaceutically active agent is capable of dissolution upon contact with a fluid such as water, stomach acid, intestinal fluid or the like. In one embodiment, the dissolution characteristics of the pharmaceutically active agent within the tablet meets USP specifications for immediate release tablets including the pharmaceutically active agent. For example, for acetaminophen tablets, USP 24 specifies that in pH 5.8 phosphate buffer, using USP apparatus 2 (paddles) at 50 rpm, at least 80% of the acetaminophen contained in the tablet is released there from within 30 minutes after dosing, and for ibuprofen tablets, USP 24 specifies that in pH 7.2 phosphate buffer, using USP apparatus 2 (paddles) at 50 rpm, at least 80% of the ibuprofen contained in the tablet is released there from within 60 minutes after dosing. See USP 24, 2000 Version, 19-20 and 856 (1999). In another embodiment, the dissolution characteristics of the pharmaceutically active agent are modified: e.g. controlled, sustained, extended, retarded, prolonged, delayed and the like.

Tablets Coatings

In one embodiment, the method of the present invention furthers includes coating the tablet (e.g., with an outer coating). In one embodiment, the method further includes coating the tablet with a subcoating prior to applying the outercoating.

Subcoating

In one embodiment, tablet contains one or more subcoating layers. In one embodiment, the subcoating layer substantially covers the surface of the tablet. The use of subcoatings is well known in the art and disclosed in, for example, U.S. Pat. No. 3,185,626, which is incorporated by reference herein. Examples of suitable subcoatings are disclosed in U.S. Pat. Nos. 4,683,256, 4,543,370, 4,643,894, 4,828,841, 4,725,441, 4,802,924, 5,630,871, and 6,274,162, which are all incorporated by reference herein. Suitable subcoatings may include one or more of the following ingredients: cellulose ethers such as hydroxypropylmethylcellulose, hydroxypropylcellulose, and hydroxyethylcellulose; polycarbohydrates such as xanthan gum, starch, and maltodextrin; plasticizers including for example, glycerin, polyethylene glycol, propylene glycol, dibutyl sebecate, triethyl citrate, vegetable oils such as castor oil, surfactants such as polysorbate-80, sodium lauryl sulfate and dioctyl-sodium sulfosuccinate; polycarbohydrates, pigments, and opacifiers.

In one embodiment, the subcoating includes, based upon the total weight of the subcoating, from about 2 percent to about 8 percent, e.g. from about 4 percent to about 6 percent of a water-soluble cellulose ether and from about 0.1 percent to about 1 percent, castor oil, as disclosed in detail in U.S. Pat. No. 5,658,589, which is incorporated by reference herein. In another embodiment, the subcoating includes, based upon the total weight of the subcoating, from about 20 percent to about 50 percent (such as from about 25 percent to about 40 percent) of HPMC; from about 45 percent to about 75 percent (such as from about 50 percent to about 70 percent) of maltodextrin; and from about 1 percent to about 10 percent (such as from about 5 percent to about 10 percent) of PEG 400.

The subcoating typically is present in an amount, based upon the dry weight of the tablet, from about 0 percent to about 5 percent. The dried dip coating layer typically is present in an amount, based upon the dry weight of the tablet and the optional subcoating, from about 1.5 percent to about 10 percent. In one embodiment the tablet is substantially free of a subcoating.

Outer-Coating

What is meant by outer-coating is the coating on the outer surface of the coated tablet. In one embodiment, the outer-coating substantially covers (e.g., covers at least 90 percent) the surface of the tablet.

The average thickness of the dried dip-coating layer typically is from about 40 to about 400 microns. However, one skilled in the art would readily appreciate without undue experimentation that the dip coating thickness may be varied in order to provide a smoother, easier to swallow, tablet or to achieve a desired dissolution profile. Moreover, the thickness of dipped film coatings may vary at different locations on the substrate depending upon its shape. For example, the thickness of the coating at an edge or corner of a substrate may be as much as 50 percent to 70 percent less than the thickness of the coating at the center of a major face of the substrate. This difference can be minimized by, for example, use of a thicker subcoating, or use of dipping compositions that result in higher weight gains on the substrate.

In embodiments wherein a thicker dip coating is desired, we have found that an effective amount of a weight gain enhancer (e.g., simethicone, polysorbate 80 and mixtures thereof) may be added to a film forming composition containing a film former and an optional thickener such as a hydrocolloid. The weight gain enhancer is used in an amount sufficient to increase the weight gain of the coating liquid, e.g. by at least about 10 percent, by at least about 20%, or by at least about 30% on a substrate when dried. The percent weight gain increase is determined based upon the difference between the total weight of the coated substrate with the coating composition including the weight gain enhancer, and the total weight of an coated equivalent substrate, which has been coated under similar processing conditions with a coating composition that does not include an effective amount of weight gain enhancer.

In one embodiment, the method further includes creating one or more openings in the subcoating in the portion of the tablet that is not coated with the outer-coating, to expose the tablet on the surface of the coated tablet, such as described in US Patent Application No. 2005/0152970.

In one embodiment, the method further includes creating one or more openings in the outer-coating to expose the tablet, not through the subcoating, as disclosed in US Patent Application No. 2005/0152970, but through the portion of the tablet containing the outer-coating. This is advantageous since the outer-coating disclosed herein is compatible with laser drilling, whereas gelatin is not compatible. Since gelatin is not compatible with laser drilling, it is necessary in tablets with such gelatin coating, to expose the subcoat before laser drilling the openings.

In one embodiment the outer-coating covers only a portion of the tablet such as only one half of the coated tablet. The other half of the tablet may contain a separate type of the outer-coating such as gelatin, or expose only the subcoat or tablet.

In certain embodiments in which modified release of the pharmaceutically active agent is desired, the pharmaceutically active agent or the compressed tablet may optionally be coated with a known release-modifying coating. This advantageously provides an additional tool for modifying the release profile of pharmaceutically active agent from the tablet. For example, the tablet may contain coated particles of one or more pharmaceutically active agents, in which the particle coating confers a release modifying function, as is well known in the art. Examples of suitable release modifying coatings for particles are described in U.S. Pat. Nos. 4,173,626; 4,863,742; 4,980,170; 4,984,240; 5,286,497; 5,912,013; 6,270,805; and 6,322,819. Commercially available modified release pharmaceutically active agents may also be employed. For example, acetaminophen particles, which are encapsulated with release-modifying polymers by a coaccervation process, may be used in the present invention. Such coaccervation-encapsulated acetaminophen is commercially available from, for example, Eurand America, Inc. or Circa Inc.

As used herein, "modified release" shall apply to the altered release or dissolution of an pharmaceutically active agent in a dissolution medium, such as gastrointestinal fluids. Types of modified release include: 1) extended release; or 2) delayed release. In general, modified release tablets are formulated to make the pharmaceutically active agent(s) available over an extended period of time after ingestion, which thereby allows for a reduction in dosing frequency compared to the dosing of the same pharmaceutically active agent(s) in a conventional tablet. Modified release tablets also permit the use of pharmaceutically active agent combinations wherein the duration of one pharmaceutically active agent may differ from the duration of another pharmaceutically active agent.

By "extended release," it is meant that, after administration, an pharmaceutically active agent is released from the tablet in a substantially continuous, regulated manner, and the time for complete release, e.g., depletion, of the pharmaceutically active agent from the tablet is longer than that associated with an immediate release tablet of the same. Types of extended release include controlled, sustained, prolonged, zero-order release, first-order release, pulsatile release and the like.

By "delayed release," it is meant that, after administration, there is at least one period of time when an pharmaceutically active agent is not being released from the tablet, e.g., the release of the pharmaceutically active agent(s) occurs at a time other than immediately following oral administration.

As used herein, "substantially coated" shall mean that less than about 20%, e.g. less than about 15%, or less than about 1.0% of the surface area of a particle is exposed, e.g. not covered, with a desired coating.

In one embodiment, the coating contains a film-forming pH-dependent polymers, such as enteric polymers. Examples of a film-forming pH-dependent polymers include, but are not limited to, enteric cellulose derivatives, such as for example hydroxypropyl methylcellulose phthalate, hydroxypropyl methylcellulose acetate succinate, cellulose acetate phthalate; natural resins, such as shellac and zein; enteric acetate derivatives such as for example polyvinylacetate phthalate, cellulose acetate phthalate, acetaldehyde dimethylcellulose acetate; and enteric acrylate derivatives such as for example polymethacrylate-based polymers such as poly(methacrylic acid, methyl methacrylate) 1:2, which is commercially available from Rohm Pharma GmbH under the tradename, EUDRAGIT S, and poly(methacrylic acid, methyl methacrylate) 1:1, which is commercially available from Rohm Pharma GmbH under the tradename, EUDRAGIT L, and mixtures thereof.

In one embodiment, the coating contains a thermoplastic film-forming water soluble polymer, such as a hydroxypropylmethylcellulose compound. An example of such a compound is "HPMC 291", which is a cellulose ether having a degree of substitution of about 1.9 and a hydroxypropyl molar substitution of 0.23, and containing, based upon the total weight of the compound, from about 29% to about 30% methoxyl groups and from about 7% to about 12% hydroxylpropyl groups. HPMC 2910 is commercially available from the Dow Chemical Company under the tradename METHOCEL E. METHOCEL E5, which is one grade of HPMC-2910 suitable for use in the present invention, has a viscosity of about 4 to 6 cps (4 to 6 millipascal-seconds) at 20 C in a 2% aqueous solution as determined by a Ubbelohde viscometer. Similarly, METHOCEL E6, which is another grade of HPMC-2910 suitable for use in the present invention, has a viscosity of about 5 to 7 cps (5 to 7 millipascal-seconds) at 20 C in a 2% aqueous solution as determined by a Ubbelohde viscometer. METHOCEL E15, which is another grade of HPMC-2910 suitable for use in the present invention, has a viscosity of about 15000 cps (15 millipascal-seconds) at 20 C in a 2% aqueous solution as determined by a Ubbelohde viscometer. As used herein, "degree of substitution" means the average number of substituent groups attached to an anhydroglucose ring, and "hydroxypropyl molar substitution" means the number of moles of hydroxypropyl per mole anhydroglucose.

In one embodiment, the coating contains a polyvinyl alcohol and polyethylene glycol copolymer. One suitable polyvinyl alcohol and polyethylene glycol copolymer for use as a tablet coating is commercially available from BASF Corporation under the tradename KOLLICOAT IR.

In one embodiment, the coating contains a modified starch. As used herein, "modified starches" for use in the tablet coating include starches that have been modified by crosslinking, chemically modified for improved stability or optimized performance, or physically modified for improved solubility properties or optimized performance. Examples of chemically-modified starches are well known in the art and typically include those starches that have been chemically treated to cause replacement of some of its hydroxyl groups with either ester or ether groups. Crosslinking, as used herein, may occur in modified starches when two hydroxyl groups on neighboring starch molecules are chemically linked. As used herein, "pre-gelatinized starches" or "instantized starches" refers to modified starches that have been pre-wetted, then dried to enhance their cold-water solubility.

Suitable modified starches for use in the tablet coating are commercially available from several suppliers such as, for example, A. E. Staley Manufacturing Company, and National Starch & Chemical Company. One suitable film forming modified starch includes the pre-gelatinized waxy maize derivative starches that are commercially available from National Starch & Chemical Company under the tradenames PURITY GUM and FILMSET, and mixtures thereof. Such waxy maize starches typically contain, based upon the total weight of the starch, from about 0 percent to about 18 percent of amylose and from about 100% to about 88% of amylopectin.

Other suitable film forming modified starches for use in the tablet coating include the hydroxypropylated starches, in which some of the hydroxyl groups of the starch have been etherified with hydroxypropyl groups, usually via treatment with propylene oxide. One example of a suitable hydroxypropyl starch that possesses film-forming properties is available from Grain Processing Company under the tradename, PURE-COTE B790.

In one embodiment, the coating contains a tapioca dextrin. Suitable tapioca dextrins for use as film formers as tablet coatings include, but are not limited to, those available from National Starch & Chemical Company under the tradenames CRYSTAL GUM or K-4484, and derivatives thereof such as modified food starch derived from tapioca, which is available from National Starch and Chemical under the tradename PURITY GUM 40, and copolymers and mixtures thereof.

In one embodiment, the coating contains a thickener. Examples of such thickeners include but are not limited to hydrocolloids (also referred to herein as gelling polymers), clays, gelling starches, and crystallizable carbohydrates, and mixtures thereof.

Examples of suitable hydrocolloids (also referred to herein as gelling polymers) for use as a tablet coating include alginates, agar, guar gum, locust bean, carrageenan, tara, gum arabic, tragacanth, pectin, xanthan, gellan, maltodextrin, galactomannan, pusstulan, laminarin, scleroglucan, gum arabic, inulin, pectin, whelan, rhamsan, zooglan, methylan, chitin, cyclodextrin, chitosan. Examples of suitable clays include smectites such as bentonite, kaolin, and laponite; magnesium trisilicate, magnesium aluminum silicate, and mixtures thereof. Examples of suitable gelling starches include acid hydrolyzed starches, and mixtures thereof. Additional suitable thickening hydrocolloids include low-moisture polymer solutions such as mixtures of gelatin and other hydrocolloids at water contents up to about 30%, such as for example those used to make "gummi" confection forms. Additional suitable thickeners include, but are not limited to, crystallizable carbohydrates.

In one embodiment of the invention, the tablet coating contains gelatin. Gelatin is a natural, thermogelling polymer. It is a tasteless and colorless mixture of derived proteins of the albuminous class, which is ordinarily soluble in warm water. Two types of gelatin—Type A and Type B—are commonly used. Type A gelatin is a derivative of acid-treated raw materials. Type B gelatin is a derivative of alkali-treated raw materials. The moisture content of gelatin, as well as its Bloom strength, composition and original gelatin processing conditions, determine its transition temperature between liquid and solid. Bloom is a standard measure of the strength of a gelatin gel, and is roughly correlated with molecular weight. Bloom is defined as the weight in grams required to move a half-inch diameter plastic plunger 4 mm into a 6.67% gelatin gel that has been held at 10 C for 17 hours. In a preferred embodiment, the flowable material is an aqueous solution including 20% 275 Bloom pork skin gelatin, 20% 250 Bloom Bone Gelatin, and approximately 60% water.

Use of Tablet

In one embodiment, the present invention features a method of treating an ailment, the method including orally administering the above-described tablet wherein the tablet includes an amount of the pharmaceutically active agent effective to treat the ailment. Examples of such ailments include, but are not limited to, pain (such as headaches, migraines, sore throat, cramps, back aches and muscle aches), fever, inflammation, upper respiratory disorders (such as cough and congestion), infections (such as bacterial and viral infections), depression, diabetes, obesity, cardiovascular disorders (such as high cholesterol, triglycerides, and blood pressure), gastrointestinal disorders (such as nausea, diarrhea, irritable bowel syndrome and gas), sleep disorders, osteoporosis, and nicotine dependence.

In one embodiment, the method is for the treatment of an upper respiratory disorder, wherein the pharmaceutically active agent is selected from the group of phenylephrine, cetirizine, loratidine, fexofenadine, diphenhydramine, dextromethorphan, chlorpheniramine, chlophedianol, and pseudoephedrine.

In this embodiment, the "unit dose" is typically accompanied by dosing directions, which instruct the patient to take an amount of the pharmaceutically active agent that may be a multiple of the unit dose depending on, e.g., the age or weight of the patient. Typically the unit dose volume will contain an amount of pharmaceutically active agent that is therapeutically effective for the smallest patient. For example, suitable unit dose volumes may include one tablet)

EXAMPLES

Specific embodiments of the present invention are illustrated by way of the following examples. This invention is not confined to the specific limitations set forth in these examples.

Example 1

Manufacture of Chlorpheniramine Maleate Tablet

A tablet containing the ingredients set forth in Table 1 providing a single immediate release dose of chlorpheniramine maleate is manufactured by an injection method as follows.

TABLE 1

| Ingredients | Mg/Tablet |
|---|---|
| Spray Dried Lactose (100 microns) | 397.5 |
| Magnesium Stearate | 2 |
| Chlorpheniramine Maleate | 0.5 |
| TOTAL | 400 |

Part A. Preparation of the Powder Blend

Spray dried lactose and magnesium stearate are delumped through a 30 mesh screen and the ingredients are mixed in a 2 qt. twin-shell blender for 5 minutes.

Part B. Preparation of the Liquid Drug Composition Containing Chlorpheniramine Maleate Approximately 250 mL of total solution is prepared at a concentration of 10 mg/mL. 2500 mg of chlorpheniramine maleate is dissolved in a 250 mL volumetric flask and diluted to volume with purified de-ionized water.

Part C: Compression and Drying of Tablet

A Manesty Betapress 16 station rotary tablet press (commercially available from Manesty Machines LTD, Liverpool, UK) equipped with round punch and die unit with a diameter of 0.250" is used to make the first tablet as a tablet. 399.5 mg of the powder (from Part A) is fed into each die of the tablet press and is tamped under compression force at approximately 2.0 kilonewtons of operating pressure. This is the pre-compression step. The liquid drug composition (from Part B) is placed into a reservoir which is connected to an automated injector suitable for delivering a solution, such as the 55310 Nano-Injector available from Stoelting Co. that is fitted to the a 100 μL syringe. The 100 μL syringe is fitted with tubing that is fed into a bracket that mounts to the die table of the rotary tablet press. The bracket contains an inlet for the tubing from the syringe and a stainless steel needle positioned over the top of each die cavity. Following the pre-compression step, the syringe injects 50 μL of the liquid drug composition (from Part B) and is then compressed at approximately 15.0 kilonewtons of compression force, and ejected from the tablet press.

The tablets from Part C are then placed onto a tray and into an oven at approximately 45° C. for 12 hours to dry any residual water from the liquid drug composition.

Example 2

Manufacture of Bi-Layer Tablet Containing Ibuprofen and Chlorpheniramine Maleate A bi-layer tablet providing a single immediate release dose of chlorpheniramine maleate (having the ingredients set forth in Table 1) in one layer and a single immediate release dose of ibuprofen (having the ingredients set forth in Table 2) in a second layer is manufactured as follows.

TABLE 2

| Ingredients | Mg/Tablet |
|---|---|
| Ibuprofen granules (115 microns) | 200 |
| Sodium starch glycolate | 12 |
| Colloidal silicon dioxide | 1 |
| TOTAL | 213 |

Part A. Preparation of the Powder Blend containing Ibuprofen

Ibuprofen and sodium starch glycolate are delumped through a 30 mesh screen and the ingredients are mixed in a 2 qt. twin-shell blender for 5 minutes. Colloidal silicon dioxide is also delumped through a 30 mesh screen and is added to the aforementioned mixture for blending for another 5 minutes. Prescreened (through a 30 mesh screen) ibuprofen and sodium starch glycolate are mixed in a 2 qt. twin shell blender for 5 minutes.

Part B: Compression and Drying of Bi-Layer Tablet

A Stokes S-2 rotary bi-layer tablet press available from K-Int'l Equipment, P.O. Box 186, Cottage Grove, Oreg. 97424 equipped with round punch and die unit with a diameter of 0.250" is used to make the first tablet. 399.5 mg of the powder blend (from Part A, Example 1) is fed into each die of the tablet press through a first feeder and is compressed under a compression force at approximately 7.0 kilonewtons of operating pressure. The liquid drug composition (from Part B, Example 1) is placed into a reservoir which is connected to an automated injector suitable for delivering solution, such as the 55310 Nano-Injector available from Stoelting Co., which is fitted to the a 100 μL (microliter) syringe. The 100 μL (microliter) syringe is fitted with tubing that is fed into a bracket that mounts to the die table of the rotary tablet press. The bracket contains an inlet for the tubing from the syringe and a stainless steel needle positioned over the top of each die cavity. Following the first compression step, the syringe injects 50 μL of the liquid drug composition.

Next, 213.0 mg of the ibuprofen blend (from Part A of Example 2) is then subsequently fed into each die of the tablet press through the second feeder and is compressed under compression force at approximately 10.0 kilonewtons of operating pressure, and ejected from the tablet press. The total tablet weight is about 613 mg. The tablets are then placed onto a tray and into an oven at approximately 45° C. for 12 hours to dry any residual water.

Example 3

Manufacture of Bi-Layer Tablet Containing Ibuprofen and Chlorpheniramine Maleate Not Requiring Driving Step A bi-layer tablet providing a single immediate release dose of chlorpheniramine maleate (having the ingredients set forth in Table 3) is manufactured as follows.

TABLE 3

| Ingredients | Mg/Tablet |
|---|---|
| Spray Dried Lactose (100 microns) | 234.4 |
| Microcrystalline Cellulose | 100 |
| Magnesium Stearate | 2 |
| Chlorpheniramine Maleate USP | 0.5 |
| Glycerin | 63.1 |
| TOTAL | 400 |

Part A. Preparation of the Powder Blend

Spray Dried Lactose, microcrystalline cellulose and magnesium stearate are delumped through a 30 mesh screen and the ingredients are mixed in a 2 qt. twin-shell blender for 5 minutes.

Part B. Preparation of Liquid Drug Composition Containing Chlorpheniramine Maleate Approximately 250 mL of total solution is prepared at a concentration of 10 mg/mL. 2500 mg of chlorpheniramine maleate is dissolved in a 250 mL volumetric flask and diluted to volume with glycerin.

Part C: Compression of Bi-Layer Tablet

A Stokes S-2 rotary bi-layer tablet press equipped with round punch and die unit with a diameter of 0.250" is used to make the first tablet as a tablet. 168.2 mg of the blend (from Part A of Example 3) is fed into each die of the tablet press through a first feeder and is compressed under a compression force at approximately 5.0 kilonewtons of operating pressure. The liquid drug composition (from Part G of Example 3) is placed into a reservoir which is connected to an automated injector suitable for delivering solution, such as the 55310 Nano-Injector available from Stoelting Co., which is fitted to the a 100 μL (microliter) syringe. The 100 μL (microliter) syringe is fitted with tubing that is fed into a bracket that mounts to the die table of the rotary tablet press. The bracket contains an inlet for the tubing from the syringe and a stainless steel needle positioned over the top of each die cavity. Following the first compression step, the syringe injects 50 μL of the liquid drug composition.

An additional 168.2 mg of the blend (from Part A of Example 3) is then subsequently fed into each die of the tablet press through the second feeder and is compressed under compression force at approximately 10.0 kilonewtons of operating pressure, and ejected from the tablet press. The total tablet weight is about 613 mg. No drying is required.

It is understood that while the invention has been described in conjunction with the detailed description thereof, that the foregoing description is intended to illustrate and not limit the scope of the invention, which is defined by the scope of the appended claims. Other aspects, advantages, and modifications are within the claims.

What is claimed is:

1. A method of manufacturing a tablet comprising a pharmaceutically active agent, said method comprising the steps of:
    (a) adding a powder comprising a pharmaceutically-acceptable carrier to a die cavity;
    (b) injecting a liquid drug composition comprising said pharmaceutically active agent into said die cavity such that said liquid drug composition contacts said powder;
    (c) adding additional powder comprising a pharmaceutically-acceptable carrier to a die cavity containing said liquid drug composition;
    (d) compressing the combination of said powder and said liquid drug composition within said die cavity to form said tablet; and
    (e) removing said tablet from said die cavity.

2. A method of claim 1, wherein the concentration of said pharmaceutically active agent is less than about 5%, by weight, of said tablet.

3. A method of claim 1, wherein the concentration of said pharmaceutically active agent is less than about 1%, by weight, of said tablet.

4. A method of claim 1, wherein the concentration of said pharmaceutically active agent is less than about 0.1%, by weight, of said tablet.

5. A method of claim 1, wherein said liquid drug composition further comprises a liquid carrier and said method further comprises the step of removing at least a portion of said liquid carrier from said tablet.

6. A method of claim 1, wherein said liquid drug composition further comprises a liquid carrier and said method further comprises the step of removing substantially all of said liquid carrier from said tablet.

7. A method of claim 1, wherein said liquid drug composition is a molten composition held above 37 degrees centigrade prior to said injection.

8. A method of claim 1, wherein said liquid drug composition is a solution of said pharmaceutically active agent.

9. A method of claim 1, wherein said liquid drug composition is a suspension of said pharmaceutically active agent, and the mean particle size of said pharmaceutically active agent is less than 100 microns.

10. A method of claim 1, wherein the powder comprises a pharmaceutically active agent.

11. A method of claim 10, wherein the powder comprises a different pharmaceutically active agent than the pharmaceutically active agent comprised within said liquid drug composition.

12. A method of claim 10, wherein the powder comprises the same pharmaceutically active agent as is comprised within said liquid drug composition.

13. A method of claim 10, wherein the pharmaceutically active agent comprised within said liquid drug composition is contained in a modified release coated particle.

14. A method of claim 1, wherein said method further comprises coating said tablet.

15. A method of claim 1, wherein said injection is delivered from a port within the die cavity.

16. A method of claim 1, wherein said injection is delivered from a port above the die cavity.

17. A method of claim 1, wherein said additional powder is different from said powder initially added to said die cavity.

18. A method of claim 1 wherein said liquid drug composition comprises a non-volatile liquid carrier and said powder comprises an adsorbent material.

19. A method of manufacturing a tablet comprising a pharmaceutically active agent, said method comprising the steps of:
(a) adding a powder to a die cavity;
(b) compressing said powder within said die cavity to form a tablet;
(c) injecting a liquid drug composition comprising said pharmaceutically active agent onto said tablet while said tablet is still within said die cavity; and
(d) removing said tablet from said die cavity.

* * * * *